United States Patent [19]

Ligonniere

[11] Patent Number: Plant 6,148

[45] Date of Patent: Apr. 12, 1988

[54] APPLE TREE CV. DALIGUY

[75] Inventor: Guy Ligonniere, Angers, France

[73] Assignee: Davodeau-Ligonniere S.C.A., Angers, France

[21] Appl. No.: 802,526

[22] Filed: Nov. 27, 1985

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—William H. Elliott, Jr.; William T. King

[57] ABSTRACT

The new variety is a Jonagold mutation having red skin color development early in the growing season.

1 Drawing Sheet

1

This invention relates to a new variety of Apple Tree cv. Daliguy, the fruit of which develops a red skin color very early in the growing season.

The new apple tree variety is a sport (mutation) of the variety Jonagold. The mutation of the parent Jonagold plant was induced by two irradiations with cobalt gamma rays. The new variety thus obtained has been shown to display homogeneous and stable characteristics in successive asexual propagation.

Daliguy differs from its parent Jonagold in that the natural intense red coloration of half the fruit surface is present under conditions in which Jonagold has no such color. The color of Jonagold is characterized as "[g]round color fairly bright yellow with some green tinges. One-third to one-half flushed and motted bright red. Short, broad, broken stripes." Bultitude, J. (1983) *Apples: A Guide to the Identification of International Varieties*, University of Washington Press, Seattle. In addition, the red distinctive coloration of fruit of Daliguy begins very early in the season, i.e. beginning in June and July.

Figure 1:
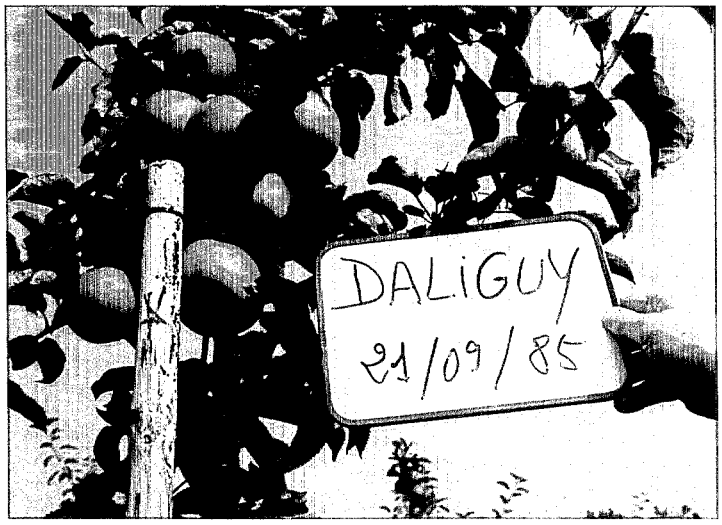
Figure 2:
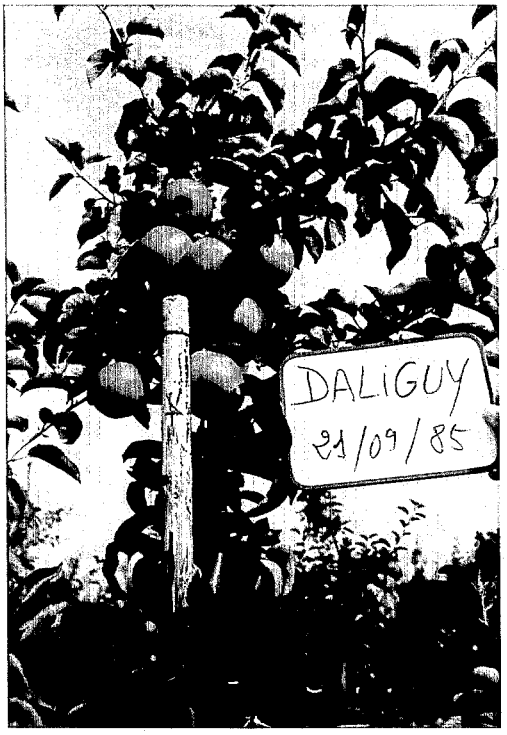
Figure 3:
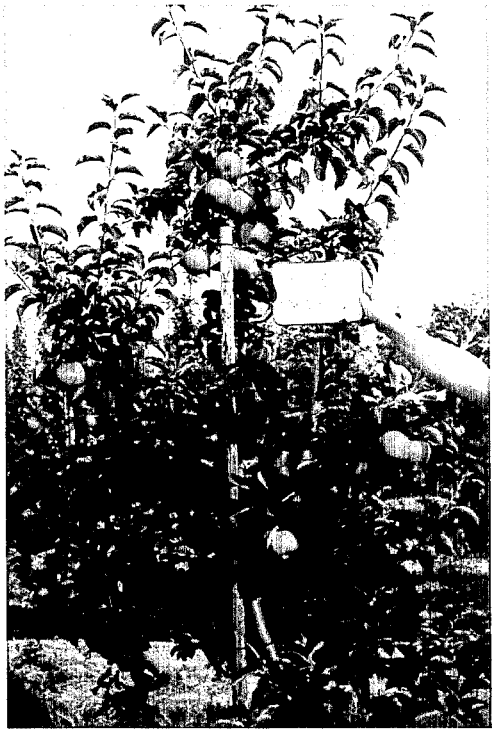

The accompanying drawings illustrates the new variety in color as grown in Lésigné, France, and shows the fruit thereof (FIGS. 1 and 2) and growth habit of the tree (FIG. 3).

The descriptive matter which follows pertains to apple trees grown in Lésigné, France, and is believed to apply to similar conditions of soil and climate elsewhere.

The following specification of the Daliguy variety utilizes the format of the Technical Questionnaire of

2

TG/14/1-Annex 3 of the *Guidelines For the Conduct of Tests for Distinctness, Homogeneity and Stability for the Apple* (*Malus Mill.*), published by the International Union for the Protection of New Varieties of Plants (UPOV). The explanation of characteristics and terminology used in the technical questionnaire of the aforesaid document are incorporated herein by reference.

| CHARACTERISTICS OF APPLE TREE CV. DALIGUY | | |
|---|---|---|
| 1. | Time of Flowering | Early, like Jonagold |
| 2. | Fruit: Size (after commercial grading of all fruits; average breadth of the greatest proportion) | Medium, like Jonagold |
| 3. | Fruit: general form | Long-conical, similar to Jonagold |
| 4. | Fruit: Type of overcolor of skin (fully mature fruit) | Red, like Jonathan |
| 5. | Fruit: form of overcolor of skin | Solid, like Richared |
| 6. | Time of maturity for picking | Early, like Jonagold, between Tydeman early Morcester and Reine des Reinettes. |

The new variety has good resistance to pests and diseases.

I claim:

1. A new and distinct variety of Apple Tree cv. Daliguy and the parts thereof, substantially as shown and described herein.

* * * * *